(12) United States Patent
Locke

(10) Patent No.: US 9,981,075 B2
(45) Date of Patent: May 29, 2018

(54) REDUCED PRESSURE TISSUE TREATMENT SYSTEMS AND METHODS HAVING A REDUCED PRESSURE DRESSING AND ASSOCIATED VALVE

(71) Applicant: KCI Licensing, Inc., San Antonio, TX (US)

(72) Inventor: Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 1196 days.

(21) Appl. No.: 13/679,865

(22) Filed: Nov. 16, 2012

(65) Prior Publication Data
US 2013/0131616 A1    May 23, 2013

Related U.S. Application Data

(60) Provisional application No. 61/563,529, filed on Nov. 23, 2011.

(51) Int. Cl.
*A61M 1/00* (2006.01)
*A61M 39/24* (2006.01)
(Continued)

(52) U.S. Cl.
CPC ........ *A61M 1/0031* (2013.01); *A61M 1/0023* (2013.01); *A61M 1/0049* (2013.01);
(Continued)

(58) Field of Classification Search
CPC .......... A61M 1/00; A61M 5/178; A61M 5/00; A61M 5/32; A61M 35/00; A61F 13/00
See application file for complete search history.

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 A1 | 8/1982 |
| AU | 745271 | 4/1999 |

(Continued)

OTHER PUBLICATIONS

Partial International Search Report for corresponding PCT/US2012/065631, dated Feb. 6, 2013.

(Continued)

*Primary Examiner* — Tatyana Zalukaeva
*Assistant Examiner* — Ilya Treyger

(57) ABSTRACT

A system for treating multiple tissue sites of a patient includes a first dressing filler adapted to be positioned at a first of the tissue sites. A second dressing filler is adapted to be positioned at a second of the tissue sites. A bridge manifold is positioned between the first tissue site and the second tissue site to provide fluid communication between the first and the second tissue site. A reduced pressure source is fluidly connected to at least one of the bridge manifold, the first tissue site, and the second tissue site. A valve is operably associated with one of the first and the second tissue sites to allow fluid to flow from the one of the first and the second tissue sites, but precluding flow towards the one of the first and the second tissue sites.

20 Claims, 7 Drawing Sheets

(51) Int. Cl.
*A61M 5/178* (2006.01)
*A61M 5/00* (2006.01)
*A61M 5/32* (2006.01)
*A61M 35/00* (2006.01)
*A61F 13/00* (2006.01)

(52) U.S. Cl.
CPC .......... *A61M 1/0088* (2013.01); *A61M 39/24* (2013.01); *A61M 1/0027* (2014.02); *A61M 2039/2466* (2013.01); *A61M 2205/18* (2013.01); *A61M 2205/84* (2013.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,493,701 A * | 1/1985 | Bootman | A61M 1/0011 222/567 |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielson | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 5,771,935 A | 6/1998 | Myers | |
| 6,071,267 A | 6/2000 | Zamierowski | |
| 6,135,116 A | 10/2000 | Vogel | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell | |
| 6,553,998 B2 | 4/2003 | Heaton et al. | |
| 6,814,079 B2 | 11/2004 | Heaton et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2011/0130712 A1 * | 6/2011 | Topaz | A61M 1/0084 604/23 |
| 2011/0144599 A1 | 6/2011 | Croizat et al. | |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 3024589 A1 * | 6/1982 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/010424 | 9/1990 |
| WO | WO 93/009727 | 5/1993 |
| WO | WO 94/020041 | 9/1994 |
| WO | WO 96/05873 | 2/1996 |
| WO | WO 97/18007 | 5/1997 |
| WO | WO 99/13793 | 3/1999 |
| WO | 2007013064 A1 | 2/2007 |

(56) References Cited

FOREIGN PATENT DOCUMENTS

| WO | WO 2009/141820 A1 | 11/2009 |
|---|---|---|
| WO | WO 2010/102146 A1 | 9/2010 |
| WO | WO 2010/142959 A1 | 12/2010 |

OTHER PUBLICATIONS

N.A. Bagautdinov, "Variant of External Vacuum Aspiration in the Treatment of Purulent Diseases of the Soft Tissues," *Current Problems in Modem Clinical Surgery: Interdepartmental Collection*, edited by V. Ye Volkov et al. (Chuvashia State University, Cheboksary, U.S.S.R. 1986);pp. 94-96 (certified translation).

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "a Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, Managing Draining Wounds and Fistulae: "New and Established Methods," *Chronic Wound Care*, edited by D. Krasner (Health Management Publications, Inc., King of Prussia, PA 1990), pp. 240-246.

G. Živadinović, V. Ðukić, Ž. Maksimović, Ð. Radak, and P. Peška, "Vacuum Therapy in the Treatment of Peripheral Blood Vessels," *Timok Medical Journal* 11 (1986), pp. 161-164 (certified translation).

F.E. Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," *British Journal of Surgery* 73 (1986), pp. 369-370.

D.E. Tribble, An Improved Sump Drain-Irrigation Device of Simple Construction, *Archives of Surgery* 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax, "Journal of the American Medical Association 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians (Jul 2007).

Examination Report for corresponding Eurpoean Application No. 12795246.3 dated May 19, 2016.

\* cited by examiner

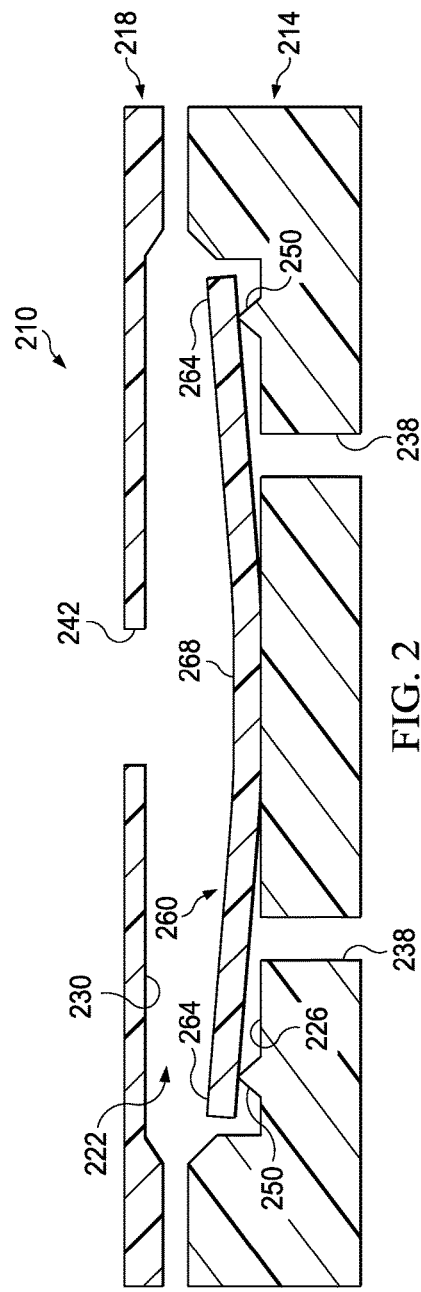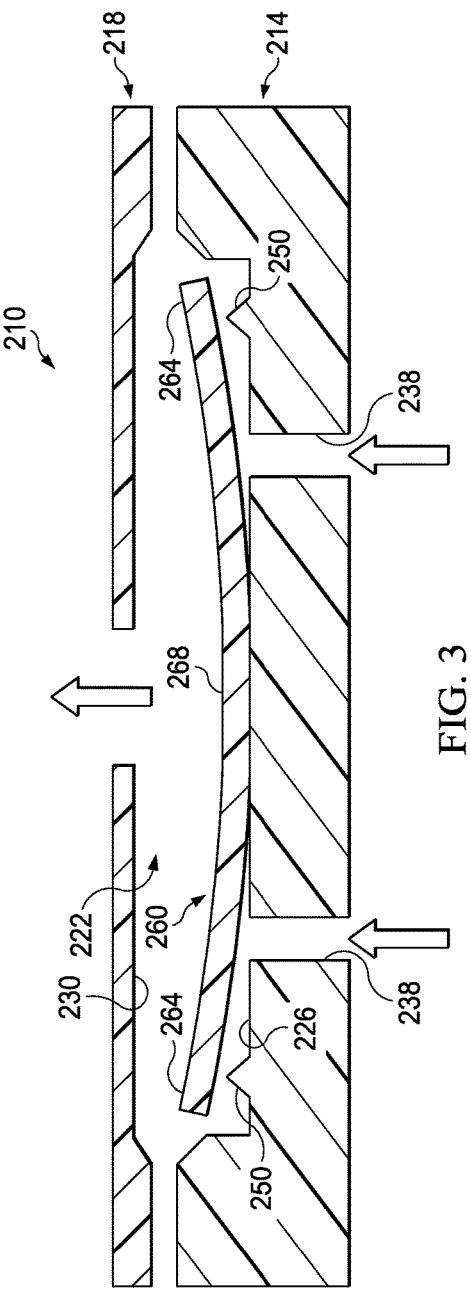

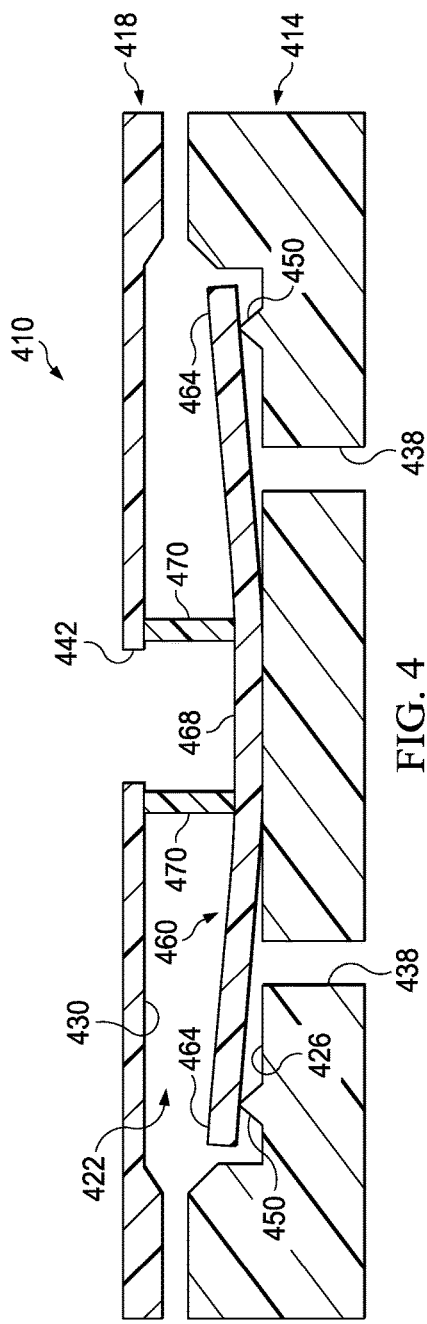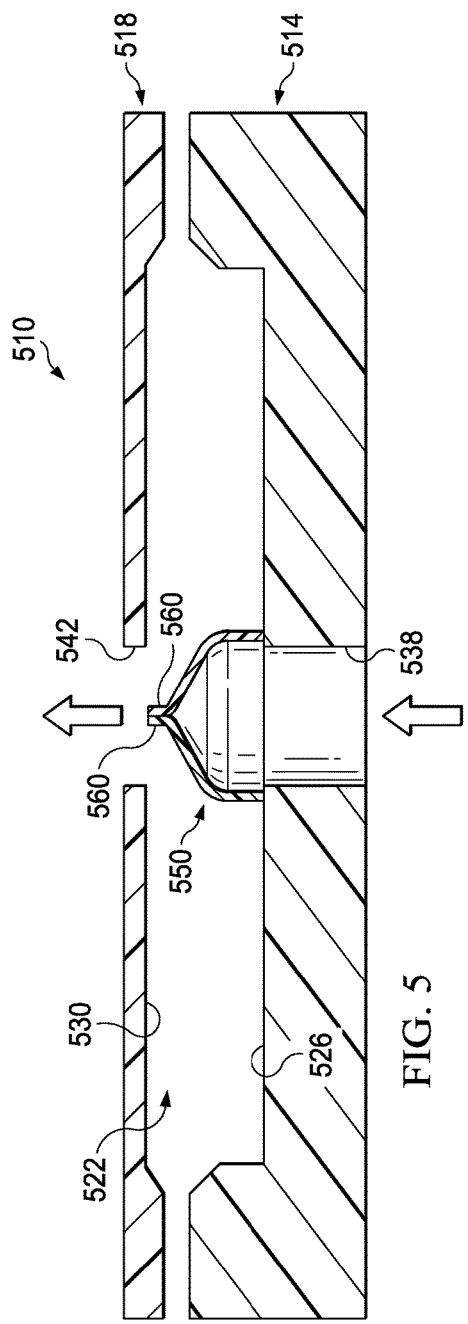

REDUCED PRESSURE TISSUE TREATMENT SYSTEMS AND METHODS HAVING A REDUCED PRESSURE DRESSING AND ASSOCIATED VALVE

CROSS-REFERENCE TO RELATED APPLICATION

This application claims priority to U.S. Provisional Patent Application No. 61/563,529 filed Nov. 23, 2011, entitled REDUCED PRESSURE TISSUE TREATMENT SYSTEMS AND METHODS HAVING A REDUCED PRESSURE DRESSING AND ASSOCIATED VALVE, the disclosure of which is hereby incorporated by reference in its entirety.

BACKGROUND

1. Field

The subject matter disclosed herein relates generally to tissue treatment systems and more particularly, but without limitation, to a reduced pressure tissue treatment system having a reduced pressure dressing and associated valve.

2. Description of Related Art

Clinical studies and practice have shown that providing a reduced pressure in proximity to a tissue site augments and accelerates the growth of new tissue at the tissue site. The applications of this phenomenon are numerous, but one particular application of reduced pressure involves treating wounds. This treatment (frequently referred to in the medical community as "negative pressure wound therapy," "reduced pressure therapy," or "vacuum therapy") provides a number of benefits, including migration of epithelial and subcutaneous tissues, improved blood flow, and microdeformation of tissue at the wound site. Together these benefits result in increased development of granulation tissue and faster healing times. Typically, reduced pressure is applied by a reduced pressure source to tissue through a porous pad or other manifold device. The porous pad contains cells or pores that are capable of distributing reduced pressure to the tissue and channeling fluids that are drawn from the tissue. The porous pad often is incorporated into a dressing having other components that facilitate treatment.

At times, it may be necessary to treat a patient having a plurality of tissue sites requiring treatment. This is particularly true of patients injured by burns, war, or other trauma. Moreover, the plurality of tissue sites may need to be treated in the field or during transportation to a hospital or other care facility.

BRIEF DESCRIPTION OF THE DRAWINGS

FIG. 2 illustrates a cross-sectional front view of a valve for use in reduced pressure treatment according to an illustrative embodiment, the valve being illustrated in a closed position;

FIG. 3 illustrates a cross-sectional front view of the valve of FIG. 2, the valve being illustrated in an open position;

FIG. 4 illustrates a cross-sectional front view of a valve for use in reduced pressure treatment according to an illustrative embodiment, the valve being illustrated in a closed position;

FIG. 5 illustrates a cross-sectional front view of a valve for use in reduced pressure treatment according to an illustrative embodiment, the valve being illustrated in a closed position;

DETAILED DESCRIPTION OF ILLUSTRATIVE EMBODIMENTS

Figure 1:
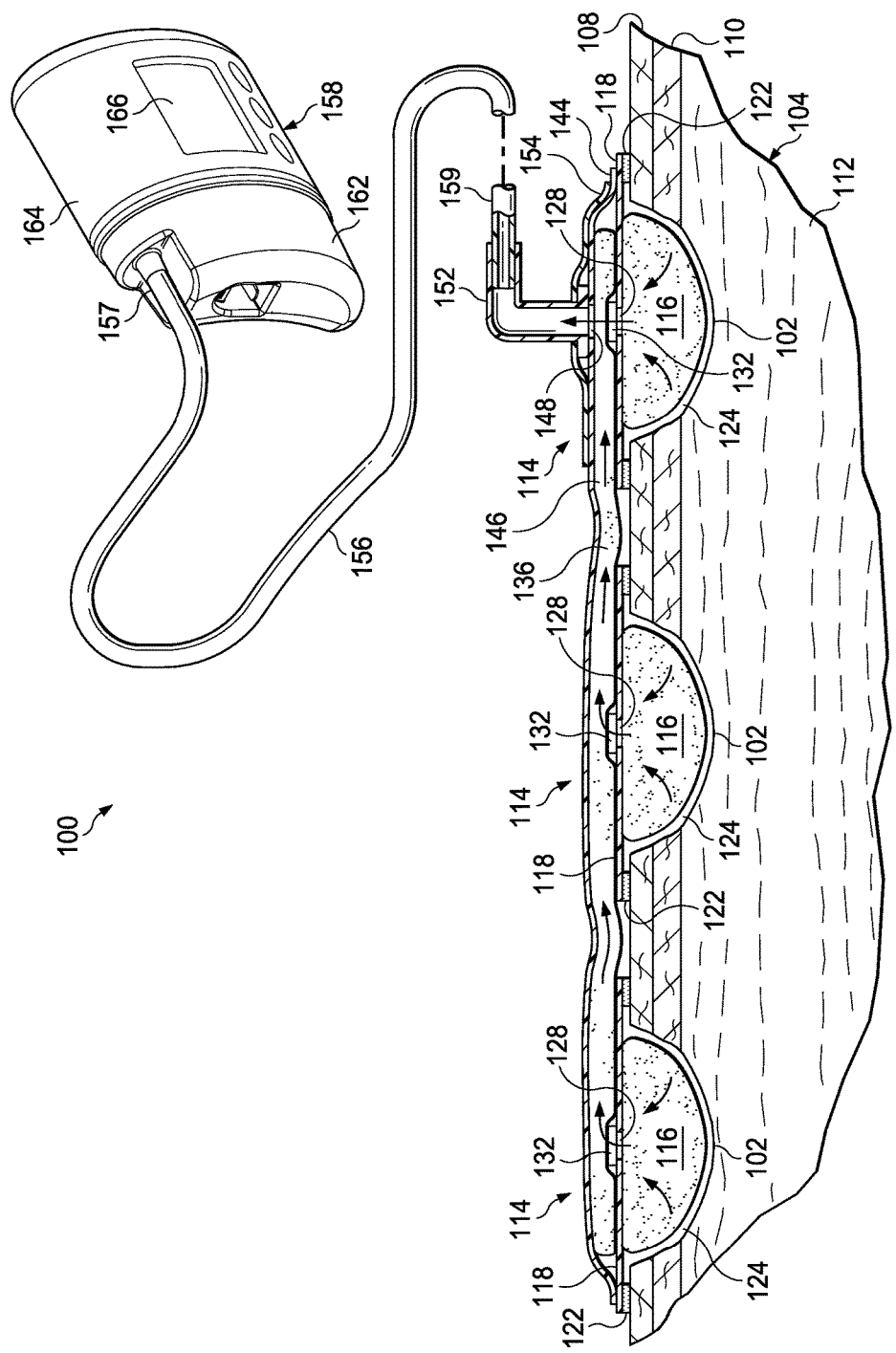
FIG. 1 illustrates a cross-sectional side view of a reduced pressure treatment system for providing treatment to multiple tissue sites of a patient according to an illustrative embodiment.

In the following detailed description, reference is made to the accompanying drawings that form a part hereof, and in which is shown by way of illustration specific embodiments in which the subject matter disclosed herein may be practiced. These embodiments are described in sufficient detail to enable those skilled in the art to practice the disclosed subject matter, and it is understood that other embodiments may be utilized and that logical, structural, mechanical, electrical, and chemical changes may be made without departing from the scope of the detailed description. To avoid detail not necessary to enable those skilled in the art to practice the embodiments described herein, the detailed description may omit certain information known to those skilled in the art. The following detailed description is, therefore, not to be taken in a limiting sense, the scope of the illustrative embodiments being defined only by the appended claims. Unless otherwise indicated, as used herein, "or" does not require mutual exclusivity.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site. Although the terms "vacuum" and "negative pressure" may be used to describe the pressure applied to the tissue site, the actual pressure reduction applied to the tissue site may be significantly less than the pressure reduction normally associated with a complete vacuum. Reduced pressure may initially generate fluid flow in the area of the tissue site. As the hydrostatic pressure around the tissue site approaches the desired reduced pressure, the flow may subside, and the reduced pressure is then maintained. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

The tissue treatment systems and methods described herein improve the treatment of a tissue site by controlling the flow of fluids (i.e. liquids and gases) to and from the tissue site. More specifically, the systems and methods include a valve or other flow control device that prevents the backflow of fluids to the tissue site. Such a system may be useful not only in the treatment of a single tissue site but also in the treatment of multiple tissue sites. When a patient has multiple tissue sites or wounds requiring simultaneous treatment, for example, it may advantageous to connect the multiple tissue sites to a single reduced pressure source. This may be achieved by (1) "bridging" the tissue sites with a manifold that is routed between the individual tissue sites and fluidly connecting the reduced pressure source to one of the bridged tissue sites, or (2) routing a separate reduced pressure tube or other conduit to each individual tissue site and then connecting the tubes to the reduced pressure source using a multi-path connector. In either of these instances, the tissue sites are each fluidly connected to a common manifold or supply conduit, which increases the likelihood of fluid drawn from one of the tissue sites entering another of the tissue sites. Cross-contamination of fluids between tissue sites is problematic, especially if infectious materials are contained at one or more of the tissue sites. These infectious materials may spread to non-infected tissue sites, thereby complicating and lengthening healing time for the patient.

The valve that is a component of the systems and methods described herein prevents cross-contamination between multiple tissue sites and prevents fluid from flowing to the tissue sites. As provided in more detail below, a number of different valve types may be used, and the positioning of the valve may vary depending on the particular treatment system. While the presence of the valve or other flow control device is particularly advantageous for treatments involving multiple tissue sites, the valve may similarly be used with single-tissue-site treatment regimens.

Referring now to the figures and primarily to FIG. 1, an illustrative embodiment of a system 100 for simultaneously treating a plurality of tissue sites 102 on a patient 104 is presented. Each tissue site 102 may be the bodily tissue of any human, animal, or other organism, including bone tissue, adipose tissue, muscle tissue, dermal tissue, vascular tissue, connective tissue, cartilage, tendons, ligaments, or any other tissue. Treatment of tissue sites 102 may include removal of fluids, e.g., exudate or ascites. While numerous tissue sites, sizes, and depths may be treated with the system 100, the system 100 may be utilized, for example, to treat wounds (not shown). A wound may extend through epidermis 108, dermis 110, and into subcutaneous tissue 112. Other depths or type of wounds or more generally tissue sites may be treated. While three tissue sites 102 are shown for illustration purposes, it should be understood that any number of tissue sites may be treated with the system 100.

The system 100 includes a plurality of reduced-pressure dressings 114 deployed on the plurality of tissue sites 102. Each of the plurality of reduced-pressure dressings 114 may be any kind of dressing that allows reduced pressure to be delivered to the tissue site 102 and that is operable to remove fluids from the tissue site 102. In one illustrative embodiment, each reduced-pressure dressing 114 includes a dressing filler, or manifold 116, and a cover or sealing member 118. The sealing member 118 is releasably coupled to the patient 104 using an attachment device 122. The attachment device 122 may take numerous forms. For example, the attachment device 122 may be a medically acceptable, pressure-sensitive adhesive that extends about a periphery or a portion of the entire sealing member 118, a double-sided drape tape, a paste, a hydrocolloid, a hydrogel, or other sealing devices or elements. For each reduced-pressure dressing 114, the sealing member 118 creates a substantially sealed space 124 containing the manifold 116 and the tissue site 102 to be treated.

For each reduced-pressure dressing 114, the manifold 116 is a substance or structure that is provided to assist in applying reduced pressure to, delivering fluids to, or removing fluids from the associated tissue site 102. The manifold 116 includes a plurality of flow channels or pathways that are capable of distributing fluids provided to or removed from the tissue site 102 around the manifold 116. In one illustrative embodiment, the flow channels or pathways are interconnected to improve distribution of fluids provided to or removed from the tissue site 102. The manifold 116 comprises one or more of the following: a biocompatible material that is capable of being placed in contact with the tissue site 102 and distributing reduced pressure to the tissue site 102; devices that have structural elements arranged to form flow channels, such as, for example, cellular foam, open-cell foam, porous tissue collections, liquids, gels, and foams that include, or cure to include, flow channels; porous materials, such as foam, gauze, felted mats, or any other material suited to a particular biological application; or porous foam that includes a plurality of interconnected cells or pores that act as flow channels, e.g., a polyurethane, open-cell, reticulated foam such as GranuFoam® material manufactured by Kinetic Concepts, Incorporated of San Antonio, Tex.; a bioresorbable material; or a scaffold material. In some situations, the manifold 116 may also be used to distribute fluids such as medications, antibacterials, growth factors, and various solutions to the tissue site 102. Other layers may be included in or on the manifold 116, such as absorptive materials, wicking materials, hydrophobic materials, and hydrophilic materials.

In one illustrative, non-limiting embodiment, the manifold 116 may be constructed from a bioresorbable material that may remain in a patient's body following use of the reduced-pressure dressing 114. Suitable bioresorbable materials may include, without limitation, a polymeric blend of polylactic acid (PLA) and polyglycolic acid (PGA). The polymeric blend may also include without limitation polycarbonates, polyfumarates, and capralactones. The manifold 116 may further serve as a scaffold for new cell-growth, or a scaffold material may be used in conjunction with the manifold 116 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

The sealing member 118 may be any material that provides a fluid seal. A fluid seal is a seal adequate to maintain reduced pressure at a desired site given the particular reduced-pressure source or subsystem involved. The sealing member 118 may be, for example, an impermeable or semi-permeable, elastomeric material. For semi-permeable materials, the permeability must be low enough that for a given reduced-pressure source, the desired reduced pressure may be maintained. The sealing member 118 may be discrete pieces for each reduced-pressure dressing 114 or may be one continuous sheet used for all the plurality of reduced-pressure dressings 114.

In the embodiment illustrated in FIG. 1, each of the sealing members 118 includes an aperture 128. The system 100 further includes a valve 132 placed over the aperture and a bridge manifold 136 positioned over the three valves 132 and dressings 114. Each valve 132, embodiments of which are discussed in more detail below with reference to FIGS. 2-6, may be sealingly attached to the corresponding sealing member 118 such that any fluid communication with the tissue site 102 must be routed through the valve 132. The bridge manifold 136 is similar in function to the manifold 116 described previously in that the bridge manifold 136 provides a manifolding capability. Indeed, the bridge manifold 136 may be made from any of the materials previously listed for manifold 116. By placing the bridge manifold 136 in fluid communication with each tissue site 102, the reduced pressure supplied to the bridge manifold 136 may be distributed to each of the tissue sites 102, thereby removing fluids from each tissue site 102 and allowing the tissue site 102 to be exposed to a reduced pressure.

A bridge cover 144 is positioned over the bridge manifold 126 and is sealed along a periphery of the bridge cover 144 to either the sealing member 118, the epidermis 108 of the patient, or in some instances both. The bridge cover 144 provides a substantially sealed space 146 within which the bridge manifold 136 resides. The presence of the bridge cover 144 allows the bridge manifold 136 to properly distribute fluids and pressures. An aperture 148 is positioned in the bridge cover 144 to provide fluid communication with the sealed space 146. While the aperture 148 is illustrated in FIG. 1 as being positioned over the right-most tissue site 102, the aperture 148 may instead be positioned over any particular tissue site 102, or alternatively may be positioned intermediately between two tissue sites.

A reduced-pressure adapter 152 is positioned over the bridge cover 144 and is fluidly connected to the sealed space 146 through the aperture 148. A separate cover 154 may be provided to seal the fluid connection between the reduced-pressure adapter 152 and the sealed space 146. The reduced-pressure adapter 152 may be any device for delivering reduced pressure to the sealed space 148. For example, the reduced-pressure adapter 152 may comprise one of the following: a T.R.A.C.® Pad or Sensa T.R.A.C.® Pad available from KCI of San Antonio, Tex.; or another device or tubing. A multi-lumen reduced-pressure delivery tube 156 or conduit is fluidly coupled to the reduced-pressure adapter 152. The multi-lumen reduced-pressure delivery tube 156 has a first end 157 and a second end 159. The first end 157 of the multi-lumen reduced-pressure delivery tube 156 is fluidly coupled to a therapy unit 158. The multi-lumen reduced-pressure delivery tube 156 includes at least one pressure-sampling lumen and at least one reduced-pressure-supply lumen. The pressure-sampling lumen provides a pressure for determining the approximate pressure within the sealed space 148, which may approximate the pressure at each tissue site 102. The reduced-pressure-supply lumen delivers the reduced pressure to the reduced-pressure dressings 114 and receives fluids therefrom. The second end 159 of the multi-lumen reduced-pressure delivery tube 156 is fluidly coupled to the reduced-pressure adapter 152.

In one embodiment, the therapy unit 158 includes a fluid containment member 162 in fluid communication with a reduced pressure source 164. In the embodiment illustrated in FIG. 1, the fluid containment member 162 is a collection canister that includes a chamber for collecting fluids from the tissue site 102. The fluid containment member 162 alternatively could be an absorbent material or any other container, device, or material that is capable of collecting fluid.

Referring still to FIG. 1, the reduced pressure source 164 may be an electrically-driven vacuum pump. In another implementation, the reduced pressure source 164 instead may be a manually-actuated or manually-charged pump that does not require electrical power. In one embodiment, the reduced pressure source 164 may be one or more piezoelectric-actuated micropumps that may be positioned remotely from the dressings 114, or adjacent the dressings 114. The reduced pressure source 164 instead may be any other type of pump, or alternatively a wall suction port or air delivery port such as those available in hospitals and other medical facilities. The reduced pressure source 164 may be housed within or used in conjunction with the therapy unit 158, which may also contain sensors, processing units, alarm indicators, memory, databases, software, display units, and user interfaces 166 that further facilitate the application of reduced pressure treatment to the tissue sites 102. In one example, pressure-detection sensors (not shown) may be disposed at or near the reduced pressure source 164. The pressure-detection sensors may receive pressure data from the reduced-pressure adapter 152 via pressure-sampling lumens in the multi-lumen reduced-pressure delivery tube 156. The pressure-detection sensors may communicate with a processing unit that monitors and controls the reduced pressure that is delivered by the reduced pressure source 164.

While the amount and nature of reduced pressure applied to a tissue site will typically vary according to the particular treatment regimen being employed, the reduced pressure will typically be between about −5 mmHg (−667 Pa) and about −500 mmHg (−66.7 kPa) and more typically between about −75 mmHg (−9.9 kPa) and about −300 mmHg (−39.9 kPa). In some embodiments, the reduced-pressure source 164 may be a V.A.C. Freedom, V.A.C. ATS, InfoVAC, ActiVAC, AbThera or V.A.C. Ulta therapy unit available through Kinetic Concepts, Inc. of San Antonio, Tex.

Referring to FIGS. 2 and 3, an illustrative embodiment of a valve 210 is presented. Valve 210 includes a valve body 214 and a valve lid 218 that are preferably formed from a polymer material, a metal, or any other material that is capable of providing a durable housing for a valve. The valve body 214 and valve lid 218 are capable of being coupled together to form an inner chamber 222. The inner chamber 222 is defined by an inlet wall 226 and an outlet wall 230. The valve body 214 includes at least one inlet port 238, and the valve lid 218 includes at least one outlet port 242. A sealing ring 250 is disposed on the inlet wall 226 and preferably surrounds the inlet port 238. While the sealing ring 250 may be an integral part of the inlet wall 226 and made from the same material as the inlet wall 226, the sealing ring 250 instead may be made from a different material that is over-molded or otherwise coupled to the inlet wall 226. In one embodiment, the sealing ring 250 may be an elastomeric or other flexible material that is bonded or otherwise coupled to the inlet wall 226.

Valve 210 further includes a valve flap 260 having a perimeter region 264 and a central region 268. The valve flap 260 may be made from a polymer or metal material, or any material that is capable of cooperating with the sealing ring 250 to control fluid flow through the valve 210. The valve flap 260 is positioned within the inner chamber 222 such that the perimeter region 264 of the valve flap 260 contacts the sealing ring 250. The central region 268 of the valve flap 260 is bonded or otherwise coupled to the inlet wall 226. While the valve flap 260 may be preformed in the curved configuration illustrated in FIGS. 2 and 3, the coupling of the valve flap 260 to the inlet wall 226 preferably requires elastic deformation of the valve flap 260. This elastic deformation of the valve flap 260 will pre-stress the valve flap 260, which creates a better seal between the valve flap 260 and the sealing ring 250.

The valve flap 260, and thus the valve 210, is illustrated in a closed position in FIG. 2. In the closed position, the valve flap 260 remains in contact with the sealing ring 250, and this contact substantially prevents fluid flow through the valve 210. In FIG. 3, the valve flap 260, and thus the valve 210, is illustrated in an open position. In the open position, the valve flap 260 is elastically deformed and no longer contacts the sealing ring 250. While the valve flap 260 is open, fluid flow is permitted through the valve 210.

In one embodiment, movement of the valve flap 260 to an open position occurs when the pressure of fluid at the inlet port 238 is greater than the pressure of fluid at the outlet port 242. This favorable pressure differential is capable of moving the valve flap 260 away from the sealing ring 250 to allow fluid flow from the inlet port 238 to the outlet port 242. Conversely, when the pressure of fluid at the outlet port 242 is greater than the pressure of fluid at the inlet port 238, the fluid exerts a biasing force on the valve flap 260 to maintain contact with the sealing ring 250. This contact with the sealing ring 250 substantially prevents fluid flow from the outlet port 242 to the inlet port 238. The continued ability of the valve flap 260 to open and close is provided by the ability of the valve flap 260 to elastically deform. This elastic deformation may be provided by the material properties and physical dimensions (i.e. thickness) of the valve flap 260.

While the sealing ring 250 is preferably continuously disposed around the at least one inlet port 238, the word "ring" is not meant to imply that the sealing ring 250 is limited to a circular shape. The sealing ring 250 could be any particular shape that is capable of fluidly isolating the inlet port 238 from the outlet port 242 when the valve flap 260 is in contact with the sealing ring 250.

The valve 210 may be used with the system 100 of FIG. 1, or any other reduced pressure treatment system, to prevent flow of fluid to a tissue site. In this manner, the valve 210 assists in preventing cross-contamination between tissue sites when multiple tissue sites are connected in serial fashion to a common reduced pressure source. Similarly, the valve 210 is capable of preventing backflow of fluid removed from a single tissue site when pressure changes may momentarily result in a differential pressure that attempts to push fluid back to the tissue site. The valve 210 may be placed adjacent a dressing similar to the placement of valves 132 relative to dressings 114 (see FIG. 1), or alternatively the valve 210 may be operably positioned relative to other system components as described herein. The valve 210 will typically be oriented such that the inlet port 238 is closer to the tissue site and the outlet port 242 is closer to the reduced pressure source.

As illustrated in FIGS. 2 and 3, movement of the valve flap 260 is dependent on the differential pressure across the valve flap 260. In one embodiment, the valve 210 may be configured to simply provide directional flow control similar to a check valve. In such a configuration, the force required to move the valve flap 260 from the closed position to the open position is relatively small. More specifically, a relatively low pressure differential across the valve flap 260 that favors flow in a direction toward the outlet port 242 would be capable of moving the valve flap 260 to the open position. In this same configuration, a relatively low pressure differential across the valve flap 260 that favors flow in a direction toward the inlet port 238 would keep the valve flap 260 in the closed position. In another embodiment, the valve flap 260 may be configured to require a higher differential pressure to move to the open position. By increasing the differential pressure required to open the valve flap 260, the valve 210 essentially becomes a regulating valve with a required "cracking pressure" to open the valve. This cracking pressure ensures that a reduced pressure reaches a particular level (i.e. that the absolute pressure be low enough) in order for the valve to open.

Referring to FIG. 4, an illustrative embodiment of a valve 410 is presented. Valve 410 includes a valve body 414 and a valve lid 418 that are preferably formed from a polymer material, a metal, or any other material that is capable of providing a durable housing for a valve. The valve body 414 and valve lid 418 are capable of being coupled together to form an inner chamber 422. The inner chamber 422 is defined by an inlet wall 426 and an outlet wall 430. The valve body 414 includes at least one inlet port 438, and the valve lid 418 includes at least one outlet port 442. A sealing ring 450 is disposed on the inlet wall 426 and preferably surrounds the inlet port 438. While the sealing ring 450 may be an integral part of the inlet wall 426 and made from the same material as the inlet wall 426, the sealing ring 450 instead may be made from a different material that is over-molded or otherwise coupled to the inlet wall 426. In one embodiment, the sealing ring 450 may be an elastomeric or other flexible material that is bonded or otherwise coupled to the inlet wall 426.

Valve 410 further includes a valve flap 460 having a perimeter region 464 and a central region 468. The valve flap 460 and the operation of valve 410 is essentially the same as valve 210 illustrated in FIGS. 2 and 3. Similar to valve flap 260, the valve flap 460 is positioned within the inner chamber 422 such that the perimeter region 464 of the valve flap 460 contacts the sealing ring 450. The central region 468 of the valve flap 460 contacts the inlet wall 426, but unlike valve 210, the valve flap 460 is not bonded or coupled to the inlet wall 426. Instead, at least one projection 470 extends from the valve lid 418. When the valve lid 418 and valve body 414 are assembled, the projection 470 exerts a force on the valve flap 460 to bias the valve flap 460 into contact with the inlet wall 426. Once again, this elastic deformation of the valve flap 460 pre-stresses the valve flap 460, which creates a better seal between the valve flap 460 and the sealing ring 450.

The valve flap 460 and thus the valve 410 is illustrated in a closed position in FIG. 4. The valve 410 operates in a manner similar to that described for valve 210, and the valve 410 may be used with the system 100 of FIG. 1, or any other reduced pressure treatment system, to prevent flow of fluid to a tissue site. In this manner, the valve 410 assists in preventing cross-contamination between tissue sites when multiple tissue sites are connected in serial fashion to a common reduced pressure source. Similarly, the valve 410 is capable of preventing backflow of fluid removed from a single tissue site when pressure changes may momentarily result in a differential pressure that attempts to push fluid back to the tissue site. The valve 410 may be placed adjacent a dressing similar to the placement of valves 132 relative to dressings 114 (see FIG. 1), or alternatively the valve 410 may be operably positioned relative to other system components as described herein. The valve 410 will typically be oriented such that the inlet port 438 is closer to the tissue site and the outlet port 442 is closer to the reduced pressure source.

Movement of the valve flap 460 is dependent on the differential pressure across the valve flap 460. In one embodiment, the valve 410 may be configured to simply provide directional flow control similar to a check valve. In such a configuration, the force required to move the valve flap 460 from the closed position to the open position is relatively small. More specifically, a relatively low pressure differential across the valve flap 460 that favors flow in a direction toward the outlet port 442 would be capable of moving the valve flap 460 to the open position. In this same configuration, a relatively low pressure differential across the valve flap 460 that favors flow in a direction toward the inlet port 438 would keep the valve flap 460 in the closed position. In another embodiment, the valve flap 460 may be configured to require a higher differential pressure to move into the open position. By increasing the differential pressure required to open the valve flap 460, the valve 410 essentially becomes a regulating valve with a required "cracking pressure" to open the valve. This cracking pressure ensures that a reduced pressure reaches a particular level (i.e. that the absolute pressure be low enough) in order for the valve 410 to open.

Referring to FIG. 5, an illustrative embodiment of a valve 510 is presented. Valve 510 includes a valve body 514 and a valve lid 518 that are preferably formed from a polymer material, a metal, or any other material that is capable of providing a durable housing for a valve. The valve body 514 and valve lid 518 are capable of being coupled together to form an inner chamber 522. The inner chamber 522 is defined by an inlet wall 526 and an outlet wall 530. The valve body 514 includes at least one inlet port 538, and the valve lid 518 includes at least one outlet port 542. A sealing member 550 is disposed on the inlet wall 526 and preferably surrounds the inlet port 538. The sealing member 550 is preferably configured in the shape of a duck-bill valve or control device and includes a pair of flappers 560 that are urged together when the valve 510 is in a closed position (see FIG. 5). The flappers 560 may be urged together by the shape and elasticity characteristics of the flappers 560. Alternatively, the flappers 560 may be urged together by a biasing member or spring device disposed internal or external to the sealing member 550.

The flappers 560 and the operation of valve 510 is similar to the operation of valves 210 and 410 illustrated in FIGS. 2-4. The valve 510 may be used with the system 100 of FIG. 1, or any other reduced pressure treatment system, to prevent flow of fluid to a tissue site. In this manner, the valve 510 assists in preventing cross-contamination between tissue sites when multiple tissue sites are connected in serial fashion to a common reduced pressure source. Similarly, the valve 510 is capable of preventing backflow of fluid removed from a single tissue site when pressure changes may momentarily result in a differential pressure that attempts to push fluid back to the tissue site. The valve 510 may be placed adjacent a dressing similar to the placement of valves 132 relative to dressings 114 (see FIG. 1), or alternatively the valve 510 may be operably positioned relative to other system components as described herein. The valve 510 will typically be oriented such that the inlet port 538 is closer to the tissue site and the outlet port 542 is closer to the reduced pressure source.

Movement of the flappers 560 is dependent on the differential pressure across the sealing member 550. In one embodiment, the valve 510 may be configured to simply provide directional flow control similar to a check valve. In such a configuration, the force required to separate the flappers 560 (i.e. move the flappers 560 to an open position) is relatively small. More specifically, a relatively low pressure differential across the sealing member 550 that favors flow in a direction toward the outlet port 542 would be capable of moving the flappers 560 to the open position. In this same configuration, a relatively low pressure differential across the sealing member 550 that favors flow in a direction toward the inlet port 538 would keep the flappers 560 in the closed position. In another embodiment, the flappers 560 may be configured to require a higher differential pressure to move into the open position. By increasing the differential pressure required to open the flappers 560, the valve 510 essentially becomes a regulating valve with a required "cracking pressure" to open the valve. This cracking pressure ensures that a reduced pressure reaches a particular level (i.e. that the absolute pressure be low enough) in order for the valve 510 to open.

Figure 6:
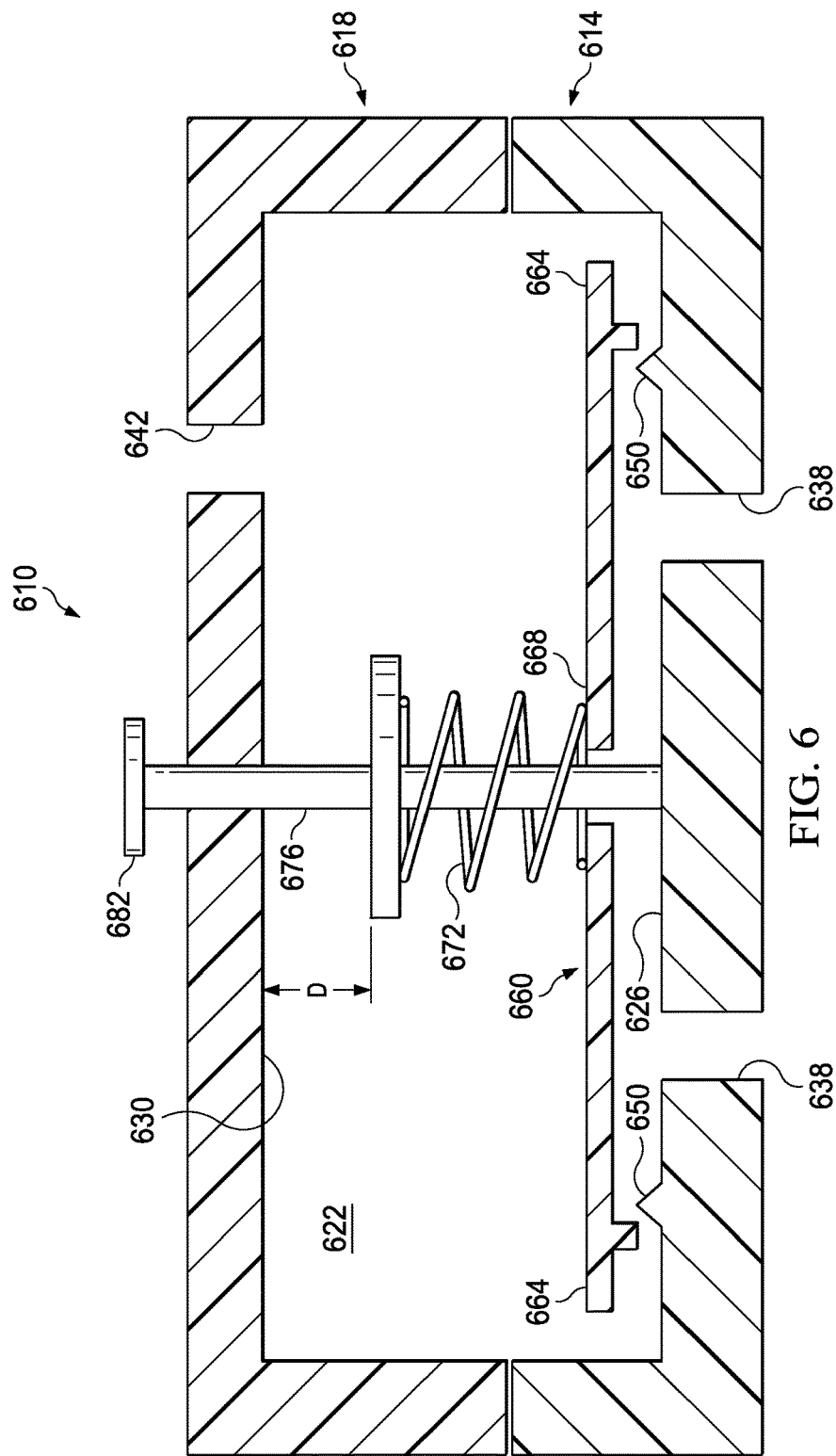
FIG. 6 illustrates a cross-sectional front view of a valve for use in reduced pressure treatment according to an illustrative embodiment, the valve being illustrated in an open position.

Referring to FIG. 6, an illustrative embodiment of a valve 610 is presented. Valve 610 includes a valve body 614 and a valve lid 618 that are preferably formed from a polymer material, a metal, or any other material that is capable of providing a durable housing for a valve. The valve body 614 and valve lid 618 are capable of being coupled together to form an inner chamber 622. The inner chamber 622 is defined by an inlet wall 626 and an outlet wall 630. The valve body 614 includes at least one inlet port 638, and the valve lid 618 includes at least one outlet port 642. A sealing ring 650 is disposed on the inlet wall 626 and preferably surrounds the inlet port 638. While the sealing ring 650 may be an integral part of the inlet wall 626 and made from the same material as the inlet wall 626, the sealing ring 650 instead may be made from a different material that is over-molded or otherwise coupled to the inlet wall 626. In one embodiment, the sealing ring 650 may be an elastomeric or other flexible material that is bonded or otherwise coupled to the inlet wall 626.

Valve 610 further includes a valve flap 660 having a perimeter region 664 and a central region 668. The valve flap 660 and the operation of valve 610 is somewhat similar to the operation of valve 210 illustrated in FIGS. 2 and 3. Similar to valve flap 260, the valve flap 660 is positioned within the inner chamber 622 such that the perimeter region 664 of the valve flap 660 contacts the sealing ring 650. However, unlike valve flap 260, valve flap 660 is not elastically deformed into a curved shape such that the central region 668 of the valve flap 660 contacts the inlet wall 626. Instead, valve flap 660 is made from a more rigid material and remains in a substantially planar configuration. The valve flap 660 is biased into contact with the sealing ring 650 in the closed position (not shown) by a spring 672. The force exerted by the spring 672 on the valve flap 660 may be adjusted by varying the distance, D, that the spring is pre-compressed. A shaft 676 and adjustment member 682 permit the distance D to be adjusted, which results in the adjustability of the force required to move the valve flap 660 to the open position (see FIG. 6).

The valve 610 operates in a manner similar to that described for valve 210, and the valve 610 may be used with the system 100 of FIG. 1, or any other reduced pressure treatment system, to prevent flow of fluid to a tissue site. In this manner, the valve 610 assists in preventing cross-contamination between tissue sites when multiple tissue sites are connected in serial fashion to a common reduced pressure source. Similarly, the valve 610 is capable of preventing backflow of fluid removed from a single tissue site when pressure changes may momentarily result in a differential pressure that attempts to push fluid back to the tissue site. The valve 610 may be placed adjacent a dressing similar to the placement of valves 132 relative to dressings 114 (see FIG. 1), or alternatively the valve 610 may be operably positioned relative to other system components as described herein. The valve 610 will typically be oriented such that the inlet port 638 is closer to the tissue site and the outlet port 642 is closer to the reduced pressure source.

Movement of the valve flap 660 is dependent on the differential pressure across the valve flap 660. In one embodiment, the valve 610 may be configured to simply provide directional flow control similar to a check valve. In such a configuration, the force required to move the valve flap 660 from the closed position to the open position is relatively small. More specifically, a relatively low pressure differential across the valve flap 660 that favors flow in a direction toward the outlet port 642 would be capable of moving the valve flap 660 to the open position. In this same configuration, a relatively low pressure differential across the valve flap 660 that favors flow in a direction toward the inlet port 638 would keep the valve flap 660 in the closed position. In another embodiment, the valve flap 660 may be configured to require a higher differential pressure to move into the open position. By increasing the differential pressure required to open the valve flap 660, the valve 610 essentially becomes a regulating valve with a required "cracking pressure" to open the valve. This cracking pressure ensures that a reduced pressure reaches a particular level (i.e. that the absolute pressure be low enough) in order for the valve 610 to open.

While multiple valve configurations have been described to regulate pressure or control the direction of fluid flow, it should be recognized that other valve configurations may be used with the reduced pressure treatment systems described herein. Other valve configurations may include, without limitation, ball valves, poppet valves, gate valves, or butterfly valves.

Figure 7:
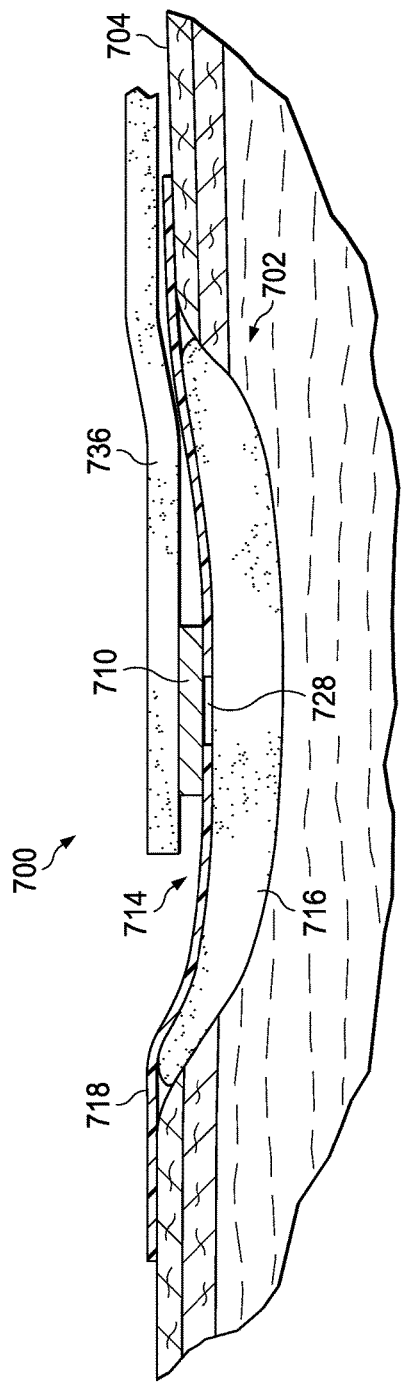
FIG. 7 illustrates a cross-sectional front view of a reduced pressure treatment system according to an illustrative embodiment, the reduced pressure treatment system having a valve operably associated with a dressing of the reduced pressure treatment system.

The positioning of the valves described herein (e.g. valves 210, 410, 510, 610) in system 100 or any other reduced pressure treatment system may vary. Referring to FIG. 7, a reduced pressure treatment system 700 includes a valve 710 positioned proximate a reduced-pressure dressing 714 positioned at a tissue site 702. The reduced-pressure dressing 714 includes a manifold 716 and a sealing member or cover 718. The cover 718 is releasably coupled to the patient 704 using adhesive or other coupling means. The cover 718 includes an aperture 728, and the valve 710 is positioned above the cover 718 such that the valve 710 covers the aperture 728. In one embodiment, the valve 710 is bonded, welded, or otherwise sealingly attached to the cover 718 such that fluids exiting the space beneath the cover 718 must pass through the valve 710. While the valve 710 is illustrated above the cover 718 in FIG. 7, the valve 710 instead may be installed beneath the cover 718 as long as the means of attachment provides the desired seal between the valve 710 and cover 718. In one embodiment, the valve 710 may include an adhesive or other bonding agent disposed on one of the surfaces of the valve 710 to allow the valve 710 to be attached to the cover 718. In another embodiment, the adhesive or bonding agent may be disposed on the cover 718.

Positioned above the valve 710 is a bridge manifold 736 similar to the bridge manifold 136 of system 100. The bridge manifold 736 provides a common means of fluid communication between multiple tissue sites, or in some circumstances, provides the ability to manifold reduced pressure from a remote location. Placement of the valve 710 in sealed contact with the cover 718 and below the bridge manifold 736 allows the valve 710 to substantially prevent fluids in the bridge manifold 736 from entering the sealed space beneath the cover 718. The placement of the valve 710, or any of the valves described herein, adjacent a reduced pressure dressing permits directional control of fluids, and in some embodiments, control of pressures associated with tissue sites undergoing reduced pressure treatment.

Figure 8:
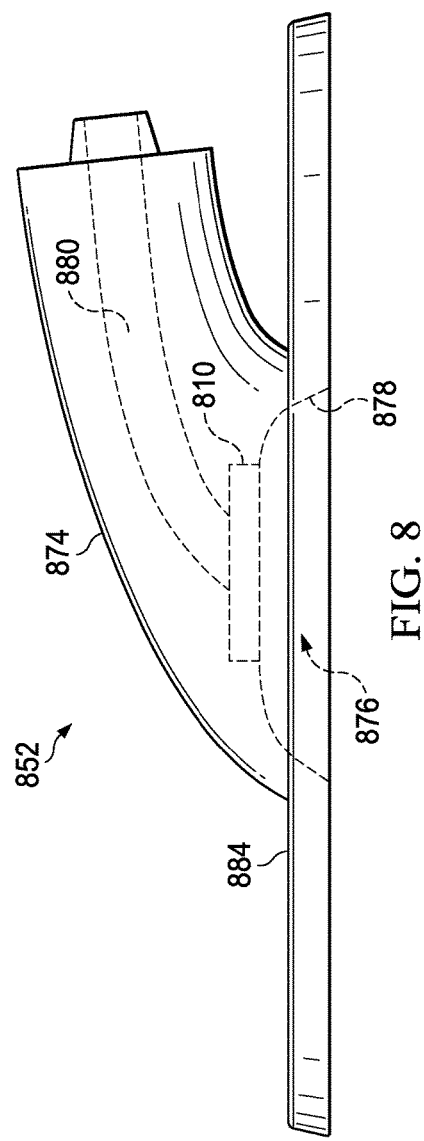
FIG. 8 illustrates a cross-sectional front view of a reduced pressure adapter for connecting a reduced pressure source to a porous pad according to an illustrative embodiment, the reduced pressure adapter having a valve for controlling fluid flow.

Referring to FIG. 8, an alternative positioning of a valve 810 is presented. In FIG. 8 a reduced-pressure adapter 852, similar to reduced-pressure adapter 152 of system 100, includes a conduit housing 874 having a recessed region 876 defining an entry surface 878. A primary conduit 880 is positioned within the conduit housing 874. The reduced-pressure adapter 852 further includes a base 884 attached to the conduit housing 874 such that an aperture of the base 884 surrounds the recessed region 876. As previously described, the reduced pressure adapter 852 provides an interface between a reduced pressure source and a reduced-pressure dressing.

In the embodiment illustrated in FIG. 8, the valve 810 is disposed between the primary conduit 880 and the recessed region 876 such that an inlet of the valve 810 is oriented toward the recessed region 876 and an outlet of the valve 810 is oriented toward the primary conduit 880. The placement of the valve 810 relative to the various components of the reduced pressure adapter 852 may vary; however, it is desired that the valve 810 be arranged such that any fluids passing through the reduced-pressure adapter 852 be required to pass through the valve 810 and be subject to control by the valve 810. The valve 810 may be permanently or removably installed relative to the reduced-pressure adapter 852.

Figure 9:
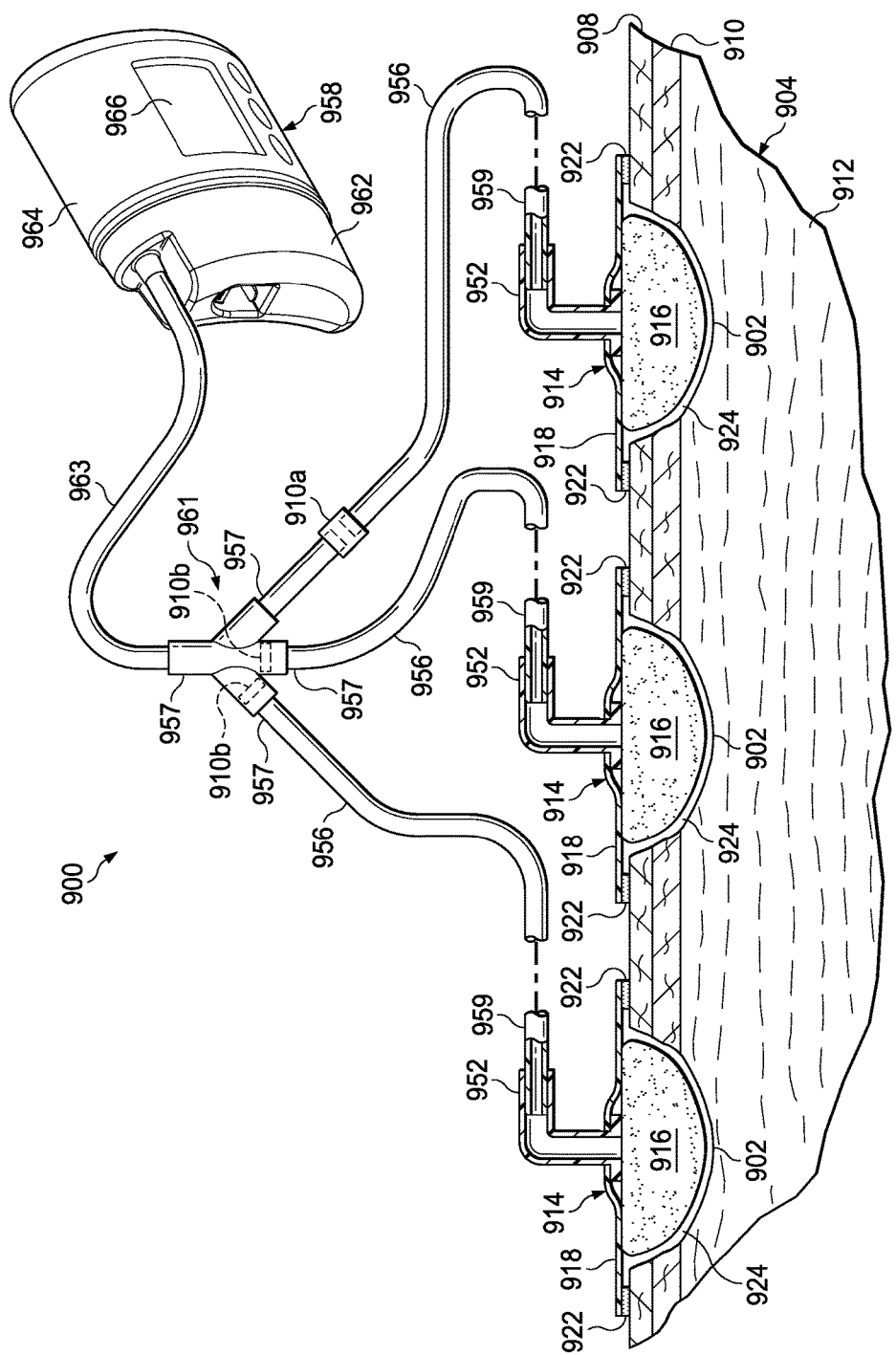
FIG. 9 illustrates a front view of a reduced pressure treatment system for providing treatment to multiple tissue sites of a patient according to an illustrative embodiment.

Referring to FIG. 9, an illustrative embodiment of a system 900 for simultaneously treating a plurality of tissue sites 902 on a patient 904 is presented. Each tissue site 902 may be the bodily tissue of any human, animal, or other organism, including bone tissue, adipose tissue, muscle tissue, dermal tissue, vascular tissue, connective tissue, cartilage, tendons, ligaments, or any other tissue. Treatment of tissue sites 902 may include removal of fluids, e.g., exudate or ascites. While numerous tissue sites, sizes, and depths may be treated with the system 900, the system 900 may, for example, be utilized to treat wounds (not shown). A wound may, for example, extend through epidermis 908, dermis 990, and into subcutaneous tissue 912. Other depths or type of wounds, or more generally, tissue sites may be treated. While three tissue sites 902 are shown for illustration purposes, it should be understood that any number of tissue sites may be treated with the system 900.

The system 900 includes a plurality of reduced-pressure dressings 914 deployed on the plurality of tissue sites 902. Each of the plurality of reduced-pressure dressings 914 may be any kind of dressing that allows reduced pressure to be delivered to the tissue site 902 and that is operable to remove fluids from the tissue site 902. In one illustrative embodiment, each reduced-pressure dressing 914 includes a dressing filler, or manifold 916, and a sealing member 918. The sealing member 918 is releasably coupled to the patient 904 using an attachment device 922. The attachment device 922 may take numerous forms. For example, the attachment device 922 may be a medically acceptable, pressure-sensitive adhesive that extends about a periphery or a portion of the entire sealing member 918, a double-sided drape tape, a paste, a hydrocolloid, a hydrogel, or other sealing devices or elements. For each reduced-pressure dressing 914, the sealing member 918 creates a substantially sealed space 924 containing the manifold 916 and the tissue site 902 to be treated.

For each reduced-pressure dressing 914, the manifold 916 is a substance or structure that is provided to assist in applying reduced pressure to, delivering fluids to, or removing fluids from the associated tissue site 902. The manifold 916 includes a plurality of flow channels or pathways that are capable of distributing fluids provided to or removed from the tissue site 902 around the manifold 916. In one illustrative embodiment, the flow channels or pathways are interconnected to improve distribution of fluids provided to or removed from the tissue site 902. The manifold 916 comprises one or more of the following: a biocompatible material that is capable of being placed in contact with the tissue site 902 and distributing reduced pressure to the tissue site 902; devices that have structural elements arranged to form flow channels, such as, for example, cellular foam, open-cell foam, porous tissue collections, liquids, gels, and foams that include, or cure to include, flow channels; porous materials, such as foam, gauze, felted mats, or any other material suited to a particular biological application; or porous foam that includes a plurality of interconnected cells or pores that act as flow channels, e.g., a polyurethane, open-cell, reticulated foam such as GranuFoam® material manufactured by Kinetic Concepts, Incorporated of San Antonio, Tex.; a bioresorbable material; or a scaffold material. In some situations, the manifold 916 may also be used to distribute fluids such as medications, antibacterials, growth factors, and various solutions to the tissue site 902. Other layers may be included in or on the manifold 916, such as absorptive materials, wicking materials, hydrophobic materials, and hydrophilic materials.

In one illustrative, non-limiting embodiment, the manifold 916 may be constructed from a bioresorbable material that may remain in a patient's body following use of the reduced-pressure dressing 914. Suitable bioresorbable materials may include, without limitation, a polymeric blend of polylactic acid (PLA) and polyglycolic acid (PGA). The polymeric blend may also include without limitation polycarbonates, polyfumarates, and capralactones. The manifold 916 may further serve as a scaffold for new cell-growth, or a scaffold material may be used in conjunction with the manifold 916 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

The sealing member 918 may be any material that provides a fluid seal. A fluid seal is a seal adequate to maintain reduced pressure at a desired site given the particular reduced pressure source or subsystem involved. The sealing member 918 may be, for example, an impermeable or semi-permeable, elastomeric material. For semi-permeable materials, the permeability must be low enough that for a given reduced-pressure source, the desired reduced pressure may be maintained. The sealing member 918 may be discrete pieces for each reduced-pressure dressing 914 or may be one continuous sheet used for all the plurality of reduced-pressure dressings 914.

In the embodiment illustrated in FIG. 9, a reduced-pressure adapter 952 is coupled to each sealing member 918 such that the reduced-pressure adapter 952 allows fluid communication with the sealed space 924 beneath each sealing member 918. The reduced-pressure adapter 952 may be any device for delivering reduced pressure to the sealed space 924. For example, the reduced-pressure adapter 952 may comprise one of the following: a T.R.A.C. Pad or Sensa T.R.A.C.® Pad available from KCI of San Antonio, Tex.; or another device or tubing. A multi-lumen reduced-pressure delivery tube 956 or conduit is fluidly coupled to each reduced-pressure adapter 952. The multi-lumen reduced-pressure delivery tube 956 has a first end 957 and a second end 959. The first end 957 of the multi-lumen reduced-pressure delivery tube 956 is fluidly coupled to a multi-path connector 961. The multi-path connector 961 illustrated in FIG. 9 includes four connection ports, one for receiving each of the reduced pressure delivery tubes 956 and one for receiving a supply tube 963 fluidly connected between the multi-path connector 961 and a therapy unit 958.

Each multi-lumen reduced-pressure delivery tube 956 may include at least one pressure-sampling lumen and at least one reduced-pressure-supply lumen. The pressure-sampling lumen provides a pressure for determining the approximate pressure within the sealed space 924, which may approximate the pressure at each tissue site 902. The reduced-pressure-supply lumen delivers the reduced pressure to the reduced-pressure dressings 914 and receives fluids therefrom. The second end 959 of the multi-lumen reduced-pressure delivery tube 956 is fluidly coupled to the reduced-pressure adapter 952.

In one embodiment, the therapy unit 958 includes a fluid containment member 962 in fluid communication with a reduced pressure source 964. In the embodiment illustrated in FIG. 9, the fluid containment member 962 is a collection canister that includes a chamber for collecting fluids from the tissue site 902. The fluid containment member 962 alternatively could be an absorbent material or any other container, device, or material that is capable of collecting fluid.

Referring still to FIG. 9, the reduced pressure source 964 may be an electrically driven vacuum pump. In another implementation, the reduced pressure source 964 instead may be a manually-actuated or manually-charged pump that does not require electrical power. In one embodiment, the reduced pressure source 964 may be one or more piezoelectric-actuated micropumps that may be positioned remotely from the dressings 914, or adjacent the dressings 914. The reduced pressure source 964 instead may be any other type of pump, or alternatively a wall suction port or air delivery port such as those available in hospitals and other medical facilities. The reduced pressure source 964 may be housed within or used in conjunction with the therapy unit 958, which may also contain sensors, processing units, alarm indicators, memory, databases, software, display units, and user interfaces 966 that further facilitate the application of reduced pressure treatment to the tissue sites 902. In one example, pressure-detection sensors (not shown) may be disposed at or near the reduced pressure source 964. The pressure-detection sensors may receive pressure data from the reduced-pressure adapter 952 via pressure-sampling lumens in the multi-lumen reduced-pressure delivery tube 956. The pressure-detection sensors may communicate with a processing unit that monitors and controls the reduced pressure that is delivered by the reduced pressure source 964.

While the amount and nature of reduced pressure applied to a tissue site will typically vary according to the particular treatment regimen being employed, the reduced pressure will typically be between about −5 mmHg (−667 Pa) and about −500 mmHg (−66.7 kPa) and more typically between about −75 mmHg (−9.9 kPa) and about −300 mmHg (−39.9 kPa). In some embodiments, the reduced-pressure source 964 may be a V.A.C. Freedom, V.A.C. ATS, InfoVAC, ActiVAC, AbThera or V.A.C. Ulta therapy unit available through Kinetic Concepts, Inc. of San Antonio, Tex.

The system 900 further includes a valve 910 associated with the fluid communication paths located between each tissue site 902 and the reduced pressure source 964. With respect to one of the tissue sites 902, the valve 910 (more specifically designated 910a) is positioned in line with the reduced-pressure delivery tube 956. With respect to the remaining tissue sites 902, the valves 910 (more specifically designated 910b) are positioned within the multi-path connector 957. Each valve 910, like the other valves described herein, may provide directional fluid control to prevent fluid from flowing to the tissue sites 902. In some embodiments, the valves 910 are provided to regulate the amount of reduced pressure provided to the tissue sites 902.

Figure 10:
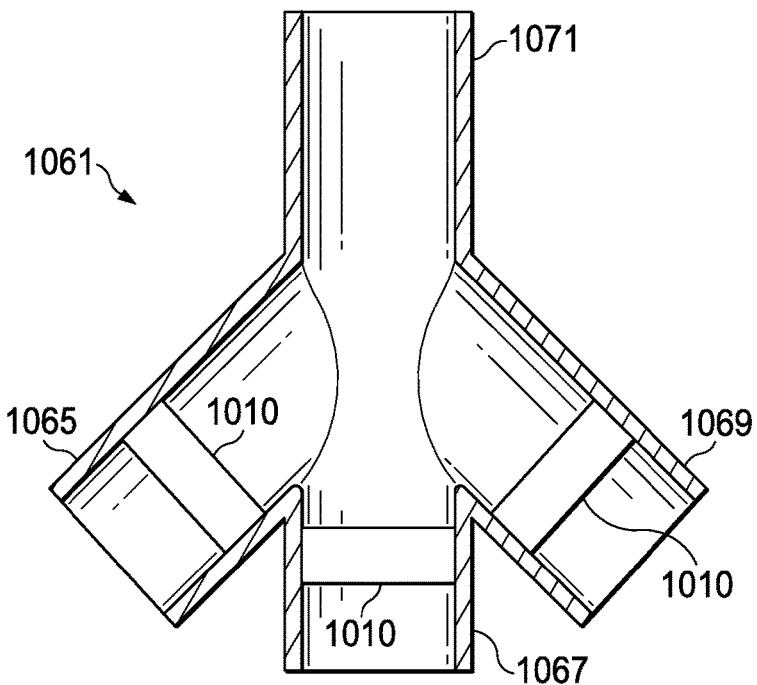
FIG. 10 illustrates a cross-sectional front view of a reduced pressure treatment system for providing treatment to multiple tissue sites of a patient according to an illustrative embodiment, the reduced pressure treatment system having a multi-path connector having a valve for controlling fluid flow.

Referring to FIG. 10, an illustrative embodiment of a multi-path connector 1061 is presented. The multi-path connector 1061 is similar to multi-path connector 961 and includes a first branch port 1065, a second branch port 1067, a third branch port 1069, and a supply port 1071. Each of the branch ports 1065, 1067, 1069 is adapted to be coupled to a reduced-pressure tube that is fluidly connected to a reduced-pressure dressing. The supply port 1071 is adapted to be coupled to a supply tube that is fluidly connected to a reduced pressure source. The multi-path connector 1061 provides a means of connecting multiple tubes or conduits so that fluid and pressure distribution may occur. While the multi-path connector 1061 illustrated in FIG. 10 is capable of fluidly connecting four conduits or tubes, a connector could instead by provided that connects a fewer number of tubes or a greater number of tubes.

In the embodiment illustrated in FIG. 10, a valve 1010 is disposed within each of the branch ports 1065, 1067, 1069. The placement of the valves 1010 relative to the various ports of the multi-path connector 1061 may vary; however, it is desired that the valve 1010 be arranged such that any fluids passing through the multi-path connector 1061 be required to pass through the valves 1010 and be subject to control by the valves 1010. The valve 1010 may be permanently or removably installed relative to the multi-path connector 1061.

Figure 11:
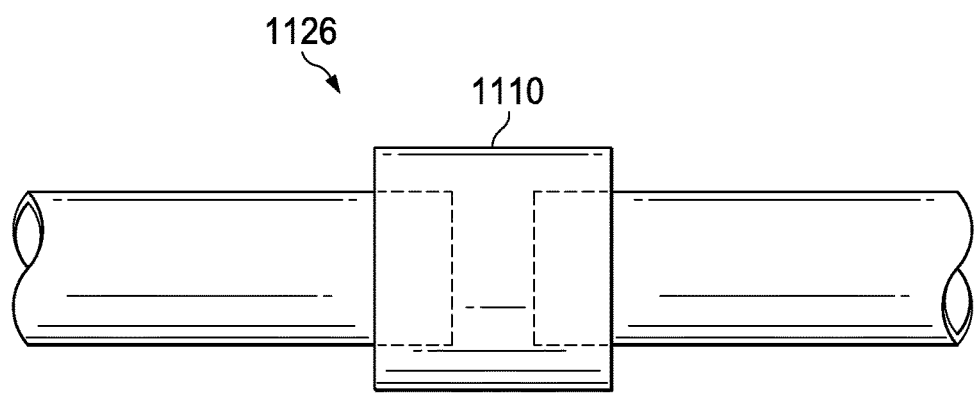
FIG. 11 illustrates a front view of a reduced pressure treatment system for providing treatment to a tissue site of a patient according to an illustrative embodiment, the reduced pressure treatment system having a reduced pressure tube operably associated with a valve for controlling fluid flow.

Referring to FIG. 11, an illustrative embodiment of a reduced-pressure delivery tube 1126 is presented. The reduced-pressure delivery tube 1126 is similar to reduced-pressure delivery tube 956 and preferably provides fluid communication between a reduced pressure source and a reduced-pressure dressing. In the embodiment illustrated in FIG. 11, a valve 1110 is operably associated with the reduced-pressure delivery tube 1126. The particular placement of the valve 1110 within or simply connected to the tube may vary; however, it is desired that the valve 1110 be arranged such that any fluids passing through the reduced-pressure delivery tube 1126 be required to pass through the valve 1110 and be subject to control by the valve 1110. The valve 1110 may be permanently or removably installed relative to the reduced-pressure delivery tube 1126.

While a number of discrete embodiments have been described, aspects of each embodiment may not be specific to only that embodiment and it is specifically contemplated that features of embodiments may be combined with features of other embodiments.

I claim:

1. A system for treating a plurality of tissue sites, the system comprising:

a first dressing filler adapted to be positioned at a first tissue site;

a second dressing filler adapted to be positioned at a second tissue site;

a bridge cover adapted to form:
 a first sealed space over the first tissue site,
 a second sealed space over the second tissue site, and
 a third sealed space containing a bridge manifold between the first sealed space formed by the bridge cover and the second sealed space formed by the bridge cover;

a first valve adapted to be associated with the first tissue site to allow fluid to flow from the first tissue site and to substantially preclude fluid flow toward the first tissue site; and a second valve adapted to be associated with the second tissue site to allow fluid to flow from the second tissue site and to substantially preclude fluid flow toward the second tissue site;

wherein the bridge manifold is adapted to provide fluid communication between the first sealed space formed by the bridge cover and the second sealed space formed by the bridge cover, wherein the first sealed space formed by the bridge cover is adapted to be fluidly coupled to a reduced pressure source, and wherein the second sealed space formed by the bridge cover is adapted to be fluidly connected to the reduced pressure source through the first sealed space formed by the bridge cover and the bridge manifold.

2. The system of claim 1, wherein fluid communication with the first dressing filler is provided through the first valve, and wherein fluid communication with the second dressing filler is provided through the second valve.

3. The system of claim 2, wherein the first valve and the second valve each have an inlet and an outlet, wherein the first valve and the second valve each are adapted to provide fluid communication from the inlet to the outlet and to substantially preclude fluid communication from the outlet to the inlet, and wherein the inlet of the first valve is positioned toward the first dressing filler and the inlet of the second valve is positioned toward the second dressing filler.

4. The system of claim 3, wherein the first valve and the second valve each have a valve flap and a sealing ring positioned in fluid communication between the inlet and the outlet, wherein the valve flap is moveable between a closed position and an open position, wherein in the closed position the valve flap contacts the sealing ring substantially precluding fluid communication between the inlet and the outlet, and wherein in open position the valve flap is separated from the sealing ring allowing fluid communication between the inlet and the outlet.

5. The system of claim 1, wherein the valve includes a valve flap and a sealing ring positioned in fluid communication between an inlet and an outlet of the valve, wherein the valve flap is moveable between a closed position and an open position, wherein in the closed position the valve flap contacts the sealing ring substantially precluding fluid communication between the inlet and the outlet, and wherein in the open position the valve flap is separated from the sealing ring allowing fluid communication between the inlet and the outlet.

6. The system of claim 5, wherein the first valve is positioned in fluid communication between the bridge manifold and the first dressing filler, and wherein the second valve is positioned in fluid communication between the bridge manifold and the second dressing filler.

7. The system of claim 1, further comprising a first cover in the first sealed space formed by the bridge cover and a second cover in the second sealed space formed by the bridge cover, wherein the first cover is adapted to be positioned adjacent the first dressing filler to provide a first sealed space formed by the first cover that is between the first cover and the first tissue site, and wherein the second cover is adapted to be positioned adjacent the second dressing filler to provide a second sealed space formed by the second cover that is between the second cover and the second tissue site.

8. The system of claim 7, wherein the first valve is sealingly attached to the first cover, and wherein the second valve is sealingly attached to the second cover.

9. The system of claim 7, further comprising an adapter adapted to fluidly couple a conduit to the first cover, wherein the first valve is housed in the adapter, and wherein the first valve is adapted to be positioned in fluid communication between the conduit and the first cover.

10. A treatment system for treating a tissue site, the system comprising:
a dressing filler adapted to be positioned at the tissue site;
a bridge cover adapted to:
be positioned adjacent the dressing filler and the tissue site to form a first sealed space between the bridge cover and the tissue site, and
form a second sealed space containing a bridge manifold, the second sealed space formed by the bridge cover is configured to cover tissue adjacent the tissue site, the bridge manifold is configured to provide fluid communication between the first sealed space formed by the bridge cover and a reduced pressure source;
the reduced pressure source adapted to be in fluid communication with the first sealed space formed by the bridge cover through the bridge manifold to provide reduced pressure to the first sealed space formed by the bridge cover; and
a valve adapted to be in fluid communication between the dressing filler and the reduced pressure source to allow fluid to flow from the tissue site while substantially preventing fluid flow toward the tissue site.

11. The system of claim 10, wherein the valve is positioned in fluid communication between the first sealed space formed by the bridge cover and the reduced pressure source, wherein fluid communication with the first sealed space formed by the bridge cover is provided through the valve.

12. The system of claim 11, wherein the valve is adapted to provide fluid communication from an inlet of the valve to an outlet of the valve, wherein the valve is adapted to substantially preclude fluid communication from the outlet of the valve to the inlet of the valve, and wherein the inlet is positioned toward the first sealed space formed by the bridge cover.

13. The system of claim 10, further comprising a conduit in fluid communication between the first sealed space formed by the bridge cover and the reduced pressure source, wherein the valve is associated with the conduit.

14. The system of claim 13, further comprising a connector fluidly coupled between a first branch of the conduit and a second branch of the conduit, wherein the valve is housed in the connector and adapted to be positioned in fluid communication between the first branch and the second branch.

15. The system of claim 10, wherein the valve is sealingly attached to the bridge cover.

16. The system of claim 10, further comprising an adapter adapted to fluidly couple a conduit to the bridge cover, wherein the valve is housed in the adapter, and wherein the valve is adapted to be positioned in fluid communication between the conduit and the bridge cover.

17. A method of applying reduced pressure treatment to a plurality of tissue sites, the method comprising:
positioning a first dressing filler at a first tissue site;
positioning a second dressing filler at a second tissue site;
positioning a bridge cover over the first dressing filler to form a first sealed space over the first tissue site, over the second dressing filler to form a second sealed space over the second tissue site, and over an area of tissue between the first tissue site and the second tissue site to form a third sealed space containing a bridge manifold, the bridge manifold configured to fluidly connect the first dressing filler to the second dressing filler;
fluidly connecting a reduced pressure source to the first dressing filler and fluidly connecting the reduced pressure source to the second dressing filler using the bridge manifold;
positioning a valve in fluid communication between the first dressing filler and the second dressing filler;
applying reduced pressure to the first dressing filler and the second dressing filler; and
substantially preventing fluid from the first tissue site from contacting the second tissue site using the valve.

18. A system for treating a plurality of tissue sites, the system comprising:
a first dressing filler adapted to be positioned at a first tissue site;
a second dressing filler adapted to be positioned at a second tissue site;
a bridge cover adapted to form a sealed space over tissue between the first dressing filler and the second dressing filler the sealed space formed by the bridge cover containing a bridge manifold configured to provide fluid communication between the first dressing filler and the second dressing filler;
a reduced pressure source adapted to be fluidly connected to the first dressing filler and the second dressing filler through the bridge manifold;
a first valve in fluid communication between the bridge manifold and the first dressing filler, wherein fluid communication with the first dressing filler is provided through the first valve; and
a second valve in fluid communication between the bridge manifold and the second dressing filler, wherein fluid communication with the second dressing filler is provided through the second valve, wherein the first valve and the second valve each have an inlet and an outlet, wherein the first valve and the second valve are each adapted to provide fluid communication from the inlet to the outlet and to substantially preclude fluid communication from the outlet to the inlet, wherein the inlet of the first valve is positioned toward the first dressing filler, and wherein the inlet of the second valve is positioned toward the second dressing filler.

19. The system of claim 18, wherein the first valve and the second valve each have a valve flap and a sealing ring positioned in fluid communication between the inlet and the outlet, wherein the valve flap is moveable between a closed position and an open position, wherein in the closed position the valve flap contacts the sealing ring substantially precluding fluid communication between the inlet and the outlet, and wherein in open position the valve flap is separated from the sealing ring allowing fluid communication between the inlet and the outlet.

20. A method of applying reduced pressure treatment to a plurality of tissue sites, the method comprising:
positioning a dressing filler at a tissue site;
positioning a bridge cover over the dressing filler and the tissue site to create a first sealed space between the bridge cover and the tissue site, and over tissue adjacent the tissue site to form a second sealed space containing a bridge manifold, the bridge manifold configure to provide fluid communication between the first sealed space formed by the bridge cover and a reduced pressure source;
fluidly connecting the reduced pressure source to the first sealed space formed by the bridge cover through the bridge manifold to provide reduced pressure to the first sealed space formed by the bridge cover;
positioning a valve in fluid communication between the dressing filler and the reduced pressure source to allow fluid to flow from the tissue site while substantially preventing fluid flow toward the tissue site; and
applying reduced pressure to the dressing filler to communicate fluid from the dressing filler, through the bridge manifold, and through the valve.

* * * * *